United States Patent
Zastrow et al.

[11] Patent Number: 5,961,988
[45] Date of Patent: *Oct. 5, 1999

[54] COSMETIC AND DERMATOLOGICAL PREPARATION BASED ON MAGNETICALLY HARD PARTICLES

[75] Inventors: Leonhard Zastrow; Karin Golz-Berner, both of Monaco, Monaco; Doucet Olivier, Nice, France

[73] Assignee: Lancaster Group GmbH, Ludwigshafen, Germany

[ * ] Notice: This patent is subject to a terminal disclaimer.

[21] Appl. No.: 09/034,734

[22] Filed: Mar. 4, 1998

[30] Foreign Application Priority Data

Apr. 10, 1997 [DE] Germany ............................ 197 15 478

[51] Int. Cl.⁶ ................................ A61K 6/00; A61K 7/00; A61K 9/00
[52] U.S. Cl. ........................... 424/400; 424/401; 514/951
[58] Field of Search .................................... 424/400, 401, 424/450

[56] References Cited

U.S. PATENT DOCUMENTS 5,800,835  9/1998  Zastrow et al. ........................ 424/647

FOREIGN PATENT DOCUMENTS 4325071  10/1995  Germany .

Primary Examiner—Thurman K. Page
Assistant Examiner—Sharon Howard
Attorney, Agent, or Firm—Collard & Roe, P.C.

[57] ABSTRACT

The invention relates to a cosmetic and dermatological preparation for treating sensitive tissue, wounds and hair. The preparation contains (a1) magnetically hard particles such as barium or strontium hexaferrite single crystals, samariumcobalt particles (SmCo) and neodymium-iron-boron particles ($Nd_2Fe_{14}B$), each with a particle size in the range of 80 to 550 nm, and with a coercive field strength of the particles in the range of 1,000 to 20,000 Oerstedt; or (a2) particles according to (a1), encapsulated in aqueous liposomes or asymmetrical lamellar aggregates, where the aggregates consist of fluorocarbons and natural phospholipids with a phosphatidylcholine content of 30 to 99 wt %; and separately in addition to (a1) or (a2) or mixtures thereof, it also contains asymmetrical lamellar aggregates without encapsulated particles which are loaded with oxygen to the saturation limit. In addition, it also contains excipients and optionally other cosmetic or pharmacological active ingredients.

10 Claims, No Drawings

COSMETIC AND DERMATOLOGICAL PREPARATION BASED ON MAGNETICALLY HARD PARTICLES

The invention relates to a new cosmetic and dermatological preparation which is especially suitable for treating sensitive tissue and fatty tissue, for treatment of wounds and for treatment of hair.

German Patent DE-C 4,325,071 discloses a circulation-enhancing preparation containing magnetically hard single-domain particles with a coercive field strength of 3000 to 5000 Oerstedt and with particle sizes in the range of 600 to 1200 nm plus cosmetic or pharmaceutical excipients. Examples of single-domain particles mentioned there as having a circulation-enhancing effect on the whole include barium and strontium hexaferrite. The single-domain particles may also be encapsulated in asymmetrical lamellar aggregates of fluorocarbons and phospholipids to facilitate penetration into the deeper layers of the skin.

The object of the invention is to greatly improve on certain properties of the known preparations.

It has now been found that a surprisingly high wound healing effect and anti-inflammatory effect can be achieved and the hair growth stimulating effect of such preparations can be increased to an unexpected extent if the particle size of the magnetically hard single-domain particles is in the range of 100 to 550 nm and if, in addition to asymmetrical lamellar aggregates charged (loaded) with single-domain particles or magnetic particles, there are asymmetrical lamellar aggregates which are completely loaded with oxygen, and the later are present in an amount of at least 2.5 wt %, preferably at least 10 wt %.

Therefore, the invention relates to a cosmetic and dermatological preparation based on magnetically hard particles and asymmetrical lamellar aggregates consisting of phospholipids and fluorocarbons, comprising of (a1) magnetically hard particles selected from the group consisting of barium hexaferrite single crystals, strontium hexaferrite single crystals, samarium cobalt particles (Smco) and neodymium iron boron particles ($Nd_2Fe_{14}B$) each with a particle size in the range of 80 to 550 nm, and the particles have a coercive field strength in the range of 1000 to 20,000 oerstedt; or (a2) magnetically hard particles according to (a1), encapsulated in aqueous liposomes or asymmetrical lamellar aggregates or a mixture of the two, where the asymmetrical lamellar aggregates consist of natural phospholipids with a phosphatidylcholine content of 30 to 99 wt % and fluorocarbons; or a mixture of (a1) and (a2); and (b) separately in addition to (a1) or (a2) or mixtures thereof, it also contains asymmetrical lamellar aggregates consisting of fluorocarbons and natural phospholipids with a phosphatidylcholine content of 30 to 99 wt %, where the asymmetrical lamellar aggregates are loaded with oxygen to the saturation limit;

(c) cosmetic or dermatological excipients; and optionally (d) cosmetic or pharmacological active ingredients.

The amount of particles according to (a1) or (a2) or mixtures thereof is in the range of 0.001 to 50 wt %, (b) is in the range of 2.5 to 70 wt %, (c) is in the range of 5.0 to 80 wt %, and optionally (d) is in the range of 0.5 to 75 wt %, based on the total weight of the preparation.

Magnetically hard particles of barium hexaferrite are preferred.

The amount of the pharmacological active ingredients is preferably in the range of 0.1 to 10 wt %, and the amount of cosmetic active ingredients is in the range of 0.5 to 75 wt %.

The fact that it is possible to reduce the particle size of the single-domain particles to 100 to 550 nm was surprising for those skilled in the art because the risk of agglomeration of such magnetic particles also increases with a reduction in particle size. Furthermore, a weaker magnetic field effect and thus a reduced efficacy were to be expected. Presumably due to the nature of the magnetic particles as single crystals (single-domain particles), however, little or no agglomeration occurs when they are mixed with asymmetrical lamellar aggregates or it does not have much effect. The magnetic field effect is in fact weaker, but nevertheless the efficacy is unexpectedly greater. Without being bound to a theory, there may be interactions with the additional asymmetrical lamellar aggregates which are loaded completely and exclusively with oxygen. However, they must be present in an amount of at least 2.5 wt %, based on the total composition, if the presumed interaction is to occur.

Depending on the fluorocarbon or fluorocarbon mixture selected, the asymmetrical lamellar aggregates are preferably loaded with oxygen up to the saturation limit, but oxygen loading may also at a lower level. A preferred partial pressure is in the range of 10 to 40 mPa (80 to 300 mm Hg), for example.

The oxygen-loaded aggregate content is preferably in the range of 10 to 50 wt %.

A preferred preparation according to this invention is one comprising (a) barium hexaferrite single crystals with a particle size in the range of 100 to 500 nm, having a coercive field strength in the range of 1000 to 4000 Oe, encapsulated in aqueous asymmetrical lamellar aggregates, in an amount of 0.01 to 10 wt %, and (b) in addition, asymmetrical lamellar aggregates which are loaded only with oxygen up to the saturation partial pressure, preferably 10 to 40 mPa (80 to 300 mm Hg), and (c) cosmetic or dermatological excipients.

Such a preferred preparation contains particles of (a) in the amount of 0.1 to 5 wt %, (b) in the amount of 5 to 30 wt %, and (c) in the amount of 0.1 to 5 wt %.

The particle size according to this invention is 80 to 550 nm for the magnetically hard particles. Small quantities of larger or smaller particles may also be present (less than 5%), but it is important that the average particle size $D_{50}$ is approximately 250 nm. This means that at least 50% of the magnetically hard particles present in an emulsion are on the order of 250 µm. An example of a typical particle size distribution according to this invention would be:

15% 80 to 100 nm,

55% 100 to 250 nm,

30% 250 to 350 nm.

The term "fluorocarbons" used here is understood to refer to perfluorinated or highly fluorinated hydrocarbon compounds or mixtures that are capable of transporting gases such as oxygen and carbon dioxide. Highly fluorinated hydrocarbon compounds in the sense of this invention are those in which most of the hydrogen atoms have been replaced by fluorine atoms, so that the ability to transport gas is not necessarily increased with further replacement. This is usually achieved when up to approximately 90% of the hydrogen atoms are replaced by fluorine atoms. In the sense of this invention, fluorocarbons in which at least 95% of the hydrogen atoms have been replaced, preferably 98% and most preferably 100%, are preferred.

A variety of fluorocarbons can be used, e.g., aliphatic linear and branched fluoroalkanes, mono- or bicyclic and optionally fluoroalkyl-substituted fluorocycloalkanes, perfluorinated aliphatic or dicyclic amines, bis(perfluoroalkyl) ethenes, perfluoropolyethers or mixtures thereof. Especially preferred are fluorocarbons such as perfluorodecalin, fluorobutyl-tetrahydrofuran, perfluorotributylamine, perfluorooctyl bromide, bisfluoro (butyl) ethene or bis-fluoro(hexyl) ethene or $C_6$–$C_9$-perfluoroalkanes.

In addition, other cosmetic or pharmacological active ingredients may also be added to the preparations according to this invention. Cosmetic active ingredients include especially vitamins, enzymes, beta-1,3-glucan, beta-1,6-glucan, carboxymethyl-glucan (e.g., CM-Glucan®), plant extracts, etc.

Especially suitable pharmacological active ingredients include heparin, acetylsalicylic acid, piroxicam, miroxicam or estrogens.

The cosmetic or pharmacological active ingredients may be present in the aqueous phase of the emulsion; they may also be contained separately in liposomes or asymmetrical lamellar aggregates such as the magnetically hard particles according to (a2). For example, acetylsalicylic acid is present in the aqueous emulsion phase and thus further increases the stability of the emulsion.

Suitable cosmetic or dermatological excipients include water, oils, emulsifiers, gels, liposomes and special components such as phospholipids, carbomer, cetearyl [sic; cetaryl] alcohol, cetyl alcohol, isopropyl myristate, isopropyl palmitate, isopropyl stearate, octyl stearate, etc.

As an additional active ingredient, the preparation may also contain to advantage kaolin according to World Patent WO96/17588, which is modified with spherical $TiO_2$ or $SiO_2$ particles with a particle size of <5 μm, where the spherical particles constitute 0.5 to 10 wt % of the kaolin mixture. The preparation thus has a very soft feeling on the skin and also has an anti-inflammatory effect.

The modified kaolin may amount to 0.1 to 6 wt %, based on the total weight of the preparation.

The preparations according to this invention are prepared by first mixing the single-domain, magnetically hard particles according to (a1) with asymmetrical lamellar aggregates at approx. 10,000 rpm and 30–35° C., and then the mixture is loaded with preferably pure oxygen up to the desired $O_2$ partial pressure. Then this is mixed with the cosmetic or dermatological excipients which may optionally already contain other active ingredients.

Another embodiment consists of the fact that first asymmetrical lamellar aggregates loaded with magnetically hard singledomain particles are prepared, with the magnetic particles with the phospholipids and the fluorocarbons as well as other additives being mixed into them. Then the asymmetrical lamellar aggregates without magnetic particles are prepared, and these aggregates are loaded with oxygen by bubbling pure oxygen through them up to saturation of the emulsion, for example. Next, the two types of aggregates are mixed together.

In the event that additional cosmetic or dermatological active ingredients are to be present in the end product, they can be accommodated together with the magnetic particles in the asymmetrical lamellar aggregates, i.e., in the perfluorocarbon which forms the interior of the aggregates. This is advantageous with substances that would crystallize in the aqueous phase. If that is not the case, e.g., with acetylsalicylic acid, they may also be accommodated in the aqueous phase of the emulsion, as explained above.

The asymmetrical lamellar aggregates themselves are prepared as follows: Natural phospholipids containing 30 to 99 wt % phosphatidylcholine are homogenized with a fluorocarbon, e.g., perfluorodecalin, at approx. 10,000 rpm. Then additives and preservatives and water are added, and the mixture is stirred again while cooling and homogenized at approx. 20,000 rpm.

The term "single-domain particles" is understood as meaning single crystals of naturally uniform magnetic orientation. Magnetically hard single-domain particles which are particularly preferred in the present invention are barium or strontium hexaferrites, which advantageously are not doped. These undoped barium or strontium hexaferrites are prepared by known processes, e.g. by growing single crystals from a tempered glass melt in accordance with the glass crystallization technique. A suitable glass for this purpose is the three-component system $BaO$—$Fe_2O_3$—$B_2O_3$, which is advantageously composed of 20 to 50% by weight of $Fe_2O_3$, 30 to 50% by weight of BaO and 20 to 50% by weight of $B_2O_3$.

The diameter/thickness ratio of the crystals of barium hexaferrite or strontium hexaferrite is generally 3:1 to 10:1.

Another effect of the composition according to this invention consists of the fact that hair growth is much greater in comparison with a preparation according to Example 18 of German Patent DE-C 4,325,071. It has unexpectedly been found that the number of hairs in the anagen phase, i.e., in the growth phase of hair, is higher by significant values of up to approx. 20% than would normally be expected. Depending on the treatment time and the amount of the magnetically hard single-domain particles and the oxygen-loaded asymmetrical lamellar aggregates, thicker hair growth and an increased amount of hair in the anagen phase in favor of the catagen phase and the telogen phase can be expected with a normal growth rate.

With regard to the anti-inflammatory effect and the wound healing effect, it has been found that a mixture of aggregates with magnetically hard particles plus aggregates with oxygen saturation yields a greatly improved anti-inflammatory effect in comparison with the pure aggregates with magnetically hard particles at the same concentration of magnetically hard particles. This effect can be further improved by the addition of certain pharmacological active ingredients. It has been found that in addition to an improvement in microcirculation achieved by the magnetically hard particles, there is also improved uptake of the active ingredients by the tissue in comparison with the effect that would otherwise be expected with this form of application, and thus a potentiated efficacy (synergism) is observed on the whole.

The oxygen-charged mixtures are introduced into the excipients or carrier materials for preparing the dispersion by gentle stirring (300–3000 rpm) and maintaining temperatures between 10 to 50° C., especially 10–14° C. for maintenance of high levels of oxygen.

The invention will be illustrated in greater detail below on the basis of examples.

EXAMPLE 1

1A) Preparing the Aggregates with Magnetically Hard Particles

The magnetically hard particles, consisting of barium hexaferrite, with an average particle size $D_{50}$ of 100 to 250 nm were homogenized in water, and carbomer was added and then the mixture was neutralized. Next, a fluorocarbon and a phospholipid with a phosphatidylcholine content of approx. 90% were added, and the mixture was homogenized. Then glycerol, propylene glycol and the preservative were added, likewise while stirring. On the whole, the temperature should not rise above 35° C.

1B) Preparing the $O_2$-saturated Aggregates

The aggregates were prepared by mixing phospholipids containing 30 to 99 wt % phosphatidylcholine with one or more fluorocarbons, e.g., with perfluorodecalin. After adding other additives such as glycerol, propylene glycol plus preservatives and water, a pure stream of oxygen is passed through the finished, homogenized, asymmetrical lamellar aggregates until reaching the saturation limit.

The aggregates containing single-domain magnetic particles can be mixed freely with the oxygen-saturated aggregates.

1C) Preparing an Emulsion with Magnetically Hard Particles

Magnetically hard particles are homogenized in water, and then an emulsion base is added. Next, the emulsions which have been mixed with the magnetic particles are combined with the oxygen-saturated, asymmetrical lamellar aggregates prepared according to Example 1B).

1D) Preparing the Preparations with Cosmetic or Pharmacological Active Ingredients The active ingredient is dissolved or suspended in water, carbomer is added, and the mixture is neutralized. Then the magnetically hard particles are added and the entire mixture is homogenized. Following this, a fluorocarbon or fluorocarbon mixture and a natural phospholipid with a high phosphatidylcholine content are added slowly and homogenized. After adding more additives and preservatives, the mixture is stirred until homogeneous.

EXAMPLE 2 Breast Cream for Hypersensitive Skin

| Phase A | |
|---|---|
| Water | Q.s. |
| Propylene glycol | 0.5% |
| Glycerol | 0.5% |
| Acrylates/$C_{10-30}$ alkyl acrylate cross polymer | 0.3% |
| Phase B | |
| Cetearyl alcohol | 2.5% |
| Cetearyl alcohol & cetyl palmitate | 1.5% |
| Octyl stearate | 1.5% |
| Phase C | |
| Triethanolamine | 0.3% |
| Preservative | 0.4% |
| Phase D | |
| Babassu oil | 1% |
| Fragrance | 0.2% |
| Aggregates according to Example 1A | 20% |
| Aggregates according to Example 1B | 10% |

Phases A and B were each heated separately to 60° C. to 70° C., phase C was mixed and neutralized. Phases A, B and C were added to phase D while stirring.

EXAMPLE 3 Hair Mask

| Phase A | |
|---|---|
| Water | Q.s. |
| Glycerol | 1% |
| Acrylates/$C_{10-30}$ alkyl acrylate cross polymer | 1% |

| Phase B | |
|---|---|
| Triethanolamine | 1% |
| Phase C | |
| Preservative | 0.3% |
| Aggregates according to Example 1A | 10% |
| Aggregates according to Example 1B | 10% |
| Melanin, soluble | 0.1% |
| Yeast extract | 1% |
| Fragreance | 0.5% |

Phase A was homogenized, phase B was neutralized, and both were added to phase C while stirring at a temperature below 40° C.

EXAMPLE 4 Heparin Ointment

| Water | Q.s. |
|---|---|
| Heparin | 1% |
| Carbomer | 2% |
| Sodium hydroxide | 2% |
| Phospholipid | 9% |
| Perfluorodecalin | 20% |
| Aggregates according to Example 1A | 2% |
| Aggregates according to Example 1B | 5% |
| glycerol | 1% |
| Preservative | 0.1% |

While stirring vigorously, heparin and the aggregates according to Example 1A were added to the perfluorodecalin, while the temperature was kept at or below 35° C. Then the other raw materials were added in the usual way. In conclusion, the aggregates according to Example 1B were added.

EXAMPLE 5 Aspirin Cream

Acetylsalicylic acid (1%) was dissolved in water while stirring well. Then the fluorocarbon was stirred with a phospholipid with a phosphatidylcholine content of 40 wt %, glycerol was added and the mixture was homogenized with water. The aspirin homogenate was added to the fluorocarbon homogenate, and the mixture was homogenized for approximately 20 minutes at a temperature below 35° C. The fluorocarbon content was 40%, the phospholipid content was 20%. Then the mixture was blended with the asymmetrical lamellar aggregates prepared according to Example 1C, constituting 8 wt % of the total mixture.

We claim:

1. A cosmetic and dermatological preparation based on magnetically hard particles and asymmetrical lamellar aggregates consisting of phospholipids and fluorocarbons, comprising of
   (a1) magnetically hard particles selected from the group consisting of barium hexaferrite single crystals, strontium hexaferrite single crystals, samarium-cobalt particles (SmCo) and neodymium-iron-boron particles ($Nd_2Fe_{14}B$), each with a particle size in the range of 80 to 550 nm, and the particles have a coercive field strength in the range of 1,000 to 20,000 Oerstedt; or
   (a2) magnetically hard particles according to (a1), encapsulated in aqueous liposomes or asymmetrical lamellar aggregates or a mixture of the two, where the asymmetrical lamellar aggregates consist of natural phospholipids with a phosphatidylcholine content of 30 to 99 wt % and fluorocarbons; or a mixture of (a1) and (a2); and (b) separately in addition to (a1) or (a2) or mixtures thereof, it also contains asymmetrical lamellar aggregates consisting of fluorocarbons and natural phospholipids having a phosphatidylcholine content of 30 to 99 wt %, where the asymmetrical lamellar aggregates are charged with oxygen to the saturation partial pressure; and (c) cosmetic or dermatological excipients or carriers; and optionally (d) cosmetic or pharmacological active ingredients; and where the amount of particles according to
(a1) or (a2) is in the range of 0.001 to 50 wt %,
(b) is in the range of 2.5 to 70 wt %,
(c) is in the range of 5 to 80 wt %, and optionally
(d) is in the range of 0.5 to 75 wt %, based on the total weight of the preparation.

2. A preparation according to claim 1, comprising
(a) barium hexaferrite single crystals with a particle size in the range of 80 to 550 nm, the particles having a coercive field strength in the range of 1000 to 5000 Oe, encapsulated in aqueous asymmetrical lamellar aggregates, in an amount of 0.01 to 10 wt % and
(b) additionally, asymmetrical lamellar aggregates which are charged only with oxygen up to the saturation partial pressure, and
(c) cosmetic or dermatological excipients.

3. A preparation according to claim 2, wherein it contains a pharmacological active ingredient selected from the group consisting of heparin, aspirin (acetylsalicylic acid), piroxicam, miroxicam and estrogens.

4. A preparation according to claim 2, wherein contains a cosmetic active ingredient selected from the group consisting of vitamins, enzymes, vitamin-enzyme mixtures from ultrasonic treatment of yeasts, beta-1,3-glucan and carboxymethyl-glucan.

5. A preparation according to claim 1, wherein the amount of asymmetrical lamellar aggregates according to claim 1(b) charged with oxygen essentially to saturation is in the range of 10 to 40 wt %.

6. A preparation according to claim 1, wherein the amount of magnetically hard single-domain particles is in the range of 0.1 to 30 wt %, especially in the range of 0.5 to 10 wt %.

7. A preparation according to claim 1, wherein the oxygen partial pressure in the charged asymmetrical lamellar aggregates is 10 to 40 mPa (180 to 300 mm Hg) after charging with oxygen.

8. Process for the manufacture of a preparation based on magnetically hard particles and asymmetrical lamellar aggregates consisting of phospholipids and fluorocarbons, comprising (a1) preparing magnetically hard particles selected from the group consisting of barium hexaferrite single crystals, strontium hexaferrite single crystals, samarium-cobalt particles (SmCo) and neodymium-iron-boron particles ($Nd_2Fe_{14}B$), each with a particle size in the range of 80 to 550 nm, and with a coercive field strength of the particles in the range of 1,000 to 20,000 Oerstedt; or (a2) preparing magnetically hard particles according to (a1), encapsulated in aqueous liposomes or asymmetrical lamellar aggregates or a mixture of the two, where the asymmetrical lamellar aggregates consist of natural phospholipids with a phosphatidylcholine content of 30 to 99 wt % and fluorocarbons; or preparing a mixture of (a1) and (a2); and (b) preparing separately in addition to (a1) or (a2) or mixtures thereof asymmetrical lamellar aggregates comprising fluorocarbons and natural phospholipids having a phosphatidylcholine content of 30 to 99 wt %, and (b1) charging said additionally prepared asymmetrical lamellar aggregates with oxygen to the saturation partial pressure and than mixing it with the aggregates prepared according to (a2) or the mixture of (a2) and (a1); or (b2) mixing the aggregates prepared according to (a2) or the mixture of (a2) and (a1) with said aggregates prepared according to (b) and than charging both with oxygen to the saturation partial pressure; and introducing the mixture prepared according to (b1) or (b2) into a cosmetically or pharmacologically acceptable excipient (c) to form a dispersion; and with the optional addition of cosmetical or pharmacological active ingredients (d) to form said dispersion;

wherein the amount of particles according to
(a1) or (a2) is in the range of 0.001 to 50 wt %,
(b) is in the range of 2.5 to 70 wt %,
(c) is in the range of 5 to 80 wt %, and optionally
(d) is in the range of 0.5 to 75 wt %, based on the total weight of said dispersion.

9. Process according to claim 8, wherein the cosmetical or pharmacological active ingredients (d) are introduced in step (a2) together with the magnetically hard particles in liposomes or asymmetric lamellar aggregates.

10. Process according to claim 8, wherein the oxygen-charged mixtures are introduced into the excipients or carrier materials for preparing said dispersion by gentle stirring and maintaining temperatures between 10 to 50° C. for maintenance of high levels of oxygen.

* * * * *